(12) United States Patent
Bouton et al.

(10) Patent No.: US 8,314,287 B2
(45) Date of Patent: Nov. 20, 2012

(54) SWITCHGRASS CULTIVAR EG1102

(75) Inventors: Joseph H. Bouton, Ardmore, OK (US); Donald T. Wood, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 465 days.

(21) Appl. No.: 12/611,779

(22) Filed: Nov. 3, 2009

(65) Prior Publication Data

US 2010/0122369 A1     May 13, 2010

Related U.S. Application Data

(60) Provisional application No. 61/112,233, filed on Nov. 7, 2008.

(51) Int. Cl.
*A01H 1/02* (2006.01)
*A01H 1/04* (2006.01)
*A01H 1/06* (2006.01)
*A01H 4/00* (2006.01)
*C12N 15/82* (2006.01)

(52) U.S. Cl. ......... 800/263; 800/266; 800/268; 800/298

(58) Field of Classification Search .............. 800/260, 800/263, 265, 267, 276, 279, 284, 290, 300, 800/301, 302, 303, 320
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 6/1996 | Hunsperger et al. | |
| 5,850,009 A | 12/1998 | Kevern | |

OTHER PUBLICATIONS

Bouton, J.H. ORNL/SUB-02-19SXV810C/01: Bioenergy Crop Breeding and Production Research in the Southeast; Final Report for 1996 to 2001; published Dec. 2002, (24 pages).*
Plant Variety Protection No. 201000049; dated Sep. 2, 2010.*
U.S. Appl. No. 61/112,233, filed Nov. 7, 2008, Bouton, Joseph H., et al.
Eshed, et al., 1996, Less-than-additive epistatic interactions of quantitative trait loci in tomato, Genetics 143:1807-1817.
Kraft, et al., 2000, Linkage disequilibrium and fingerprinting in sugar beet, Theor. App. Genet., 101:323-326.
Poehlman, J.M. and Sleper, D.A., Methods in Plant Breeding, Breeding Field Crops, 4th Ed. (1995), Iowa State University Press, pp. 172-174.
Goldman, et al., 1994, Molecular Markers Associated with Maize Kernel Oil Concentration in an Illinois High Protein x Illinois Low Protein Cross, Crop Sci., 34: 908-915.
Missaoui, A.M., et al., The effects of low plant density on response to selection for biomass production in switchgrass, Euphytica, 142: 1-12 (2005).
Bouton, J. H., Bioenergy Crop Breeding and Production Research in the Southeast, Final Report for 1996 to 2001, University of Georgia, Environmental Sciences Division, Dec. 2002.
Bouton, J. H., Improving Switchgrass as a Bioenergy Crop for the Southeastern USA, Proceedings of the 2004 Conference of the American Forage and Grassland Council, 13, 348-351, Jun. 12-16, 2004.
Anderson, W. F., Current Assessment of Dedicated Bioenergy Feedstock Crops for Southeastern United States, Proceedings 61$^{st}$ Southern Pasture & Forage Crop Improvement Conference, 2007.
CPVO Database, CPVR Application 20101557 of University of Georgia Research Foundation, Inc., filed Aug. 2, 2010.
US PVP Database, Application No. 201000049 of University of Georgia Research Foundation, Inc., filed Nov. 16, 2009.

* cited by examiner

*Primary Examiner* — Russell Kallis
(74) *Attorney, Agent, or Firm* — Jondle & Associates, P.C.

(57) ABSTRACT

A switchgrass cultivar designated EG1102 is disclosed. The invention relates to the seeds of switchgrass cultivar EG1102, to the plants of switchgrass EG1102, to plant parts of switchgrass cultivar EG1102 and to methods for producing a switchgrass plant produced by crossing switchgrass cultivar EG1102 with itself or with another switchgrass variety. The invention also relates to methods for producing a switchgrass plant containing in its genetic material one or more transgenes and to the transgenic switchgrass plants and plant parts produced by those methods. This invention also relates to switchgrass cultivars or breeding cultivars and plant parts derived from switchgrass variety EG1102, to methods for producing other switchgrass cultivars, lines or plant parts derived from switchgrass cultivar EG1102 and to the switchgrass plants, varieties, and their parts derived from use of those methods. The invention further relates to hybrid switchgrass seeds, plants and plant parts produced by crossing the cultivar EG1102 with another switchgrass cultivar.

25 Claims, No Drawings

SWITCHGRASS CULTIVAR EG1102

CROSS REFERENCE

This application claims the benefit of U.S. Provisional Application No. 61/112,233 filed Nov. 7, 2008, the specification of which is incorporated by reference in its entirety.

STATEMENT AS TO FEDERALLY SPONSORED RESEARCH

This invention was made with United States Government support under contract No. DE-AC05-00OR22725 awarded by the United States Department of Energy. The United States Government may have certain rights in this invention.

TECHNICAL FIELD

The invention relates to Switchgrass (*Panicum virgatum* L.) plants having a novel combination of increased biomass, increased disease resistance, and improved spring re-growth in comparison to similar known varieties as well as materials and methods for making such plants. All publications cited in this application are herein incorporated by reference in their entirety.

BACKGROUND OF THE INVENTION

Described herein is a new and distinctive switchgrass variety, designated EG1102. This variety is also known by the breeder identifier NFSG-992.

Switchgrass is a warm season perennial grass and is one of the dominant species of the central North American tallgrass prairie. Switchgrass can be found in remnant prairies, along roadsides, pastures and as an ornamental plant in gardens. Other common names for this grass include tall panic grass, Wobsqua grass, lowland switchgrass, blackbent, tall prairiegrass, wild redtop and thatchgrass. Switchgrass is a hardy, perennial rhizomatous grass which begins growth in late spring. It is typically shorter than Big Bluestem grass or Indiangrass. Switchgrass is used as pasture forage plant, as ground cover to control erosion and as a livestock feed.

Switchgrass uses C4 carbon fixation, giving it an advantage in conditions of drought and high temperature. The deep roots of switchgrass advantageously sequester large amounts of carbon (McLaughlin and Kszos, 2005 "Development of switchgrass (*Panicum virgatum*) as a bioenergy feedstock in the United States." *Biomass Bioenergy* 28:515-535). Once established switchgrass is also tolerant of flooding and grows rapidly, capturing a significant amount of solar energy and turning it into stored energy in the form of lignocellulosic components.

Switchgrass is often considered a good candidate for biofuel, especially ethanol fuel, production due to its hardiness against soil and climate conditions, rapid growth and low fertilization and herbicide requirements. Switchgrass offers important advantages as an energy crop, in part because it can be liquified, gasified, or burned directly. Ethanol production from switchgrass can provide as much as twenty times more net energy output than corn and removes considerably more $CO_2$ from the air.

Combustion of switchgrass pellets can result in only 3% to 4% of original mass remaining as ash due in part to switchgrass' lower silica and chloride content as compared to cool season grasses. Ash contents can be further reduced by allowing switchgrass to overwinter in the field, thereby reducing the silica and chloride contents further through the process of leaching.

Despite the many advantages that switchgrass has as a crop for food, feed or energy, in order for this grass to fulfill its promise, new varieties of switchgrass are needed. For the most part, existing varieties do not differ from the wild populations from which they are derived. What intentional breeding has occurred has focused on improving switchgrass as a forage plant, i.e., palatability and nutrition. The goal of plant breeders is to combine in a single variety an improved combination of desirable traits from the parental germplasm.

Choice of breeding or selection methods depends on the mode of plant reproduction, the heritability of the trait(s) being improved, and the type of cultivar used commercially (e.g., $F_1$ hybrid cultivar, pureline cultivar, etc.). Popular selection methods commonly include population formation by hybridization, genomic selection, marker assisted selection, recurrent selection, mutation breeding, single-seed descent, bulk selection, pedigree selection, modified pedigree selection, and mass selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are tested and compared to appropriate standards in environments representative of the commercial target area(s) for one or more years. The best lines are candidates for new commercial cultivars; those still deficient in a few traits may be used as parents to produce new populations for further selection.

These processes, which lead to the final step of marketing and distribution, usually take years from the time the first cross or selection is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar.

The goal of switchgrass plant breeding is to develop new switchgrass cultivars and hybrids. The breeder initially selects and/or crosses two or more parental lines, followed by repeated population selection, producing many new genetic combinations. The breeder can theoretically generate billions of different genetic combinations via crossing and mutations.

Each year, the plant breeder selects the germplasm to advance to the next generation during the process of development of a new cultivated variety. This germplasm is grown under unique and different geographical, climatic and soil conditions and further selections are then made during and at the end of the growing season. The cultivars that are developed are unpredictable because the breeder's selection occurs in unique environments with no control at the DNA level (using conventional breeding procedures), and with millions of different possible genetic combinations being generated. A breeder of ordinary skill in the art cannot predict the final resulting lines he develops, except possibly in a very gross and general fashion. This unpredictability results in the expenditure of large amounts of research monies to develop superior new switchgrass cultivars.

The development of new switchgrass cultivars requires the development and selection of switchgrass varieties, the crossing of these varieties and selection of superior lines. Additional data on parental lines, as well as the phenotype of the hybrid, influence the breeder's decision whether to continue using specific parents in a breeding program.

Mass and recurrent selections can be used to improve populations of either self- or cross-pollinating crops. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, switchgrass breeders commonly harvest one or more inflorescence from each plant in a population and thresh them together to form a bulk. Part of the bulk is used to plant the next generation and part is put in reserve. The procedure has been referred to as modified single-seed descent or the inflorescence-bulk technique.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs). Molecular markers can be used in marker assisted breeding for one or more traits, for genomic selection, or to generate a chromosome map that can be used in breeding to identify quantitative trait loci or map particular genes.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Switchgrass is an important and valuable crop. Thus, an important and ongoing goal of switchgrass plant breeders is to develop stable, high biomass yielding, biofuel conversion efficient cultivars that are agronomically sound. To accomplish this goal, the switchgrass breeder must select and develop switchgrass plants that have traits that result in new cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to the invention, there is provided a new switchgrass variety designated EG1102. This invention thus relates to the seeds of switchgrass variety EG1102, to the plants of switchgrass variety EG1102 and to methods for producing a switchgrass plant produced by crossing the switchgrass variety EG1102 with itself or another switchgrass variety, and the creation of variants by mutagenesis or transformation of switchgrass variety EG1102.

In another aspect, the variety described herein relates to one or more genetic polymorphisms associated with a population of switchgrass cultivar designated EG1102. The variety described herein also relates to methods for determining whether one or more genetic polymorphisms are correlated to the population.

The variety described herein also relates to methods of breeding plants using the switchgrass variety EG1102. Thus, any such methods using the switchgrass variety EG1102 are envisioned: selling, backcrosses, hybrid production, crosses to populations, and the like. All plants produced using switchgrass variety EG1102 as at least one parent are within the scope of the variety described herein. Advantageously, the switchgrass variety could be used in crosses with other, different, switchgrass plants to produce first generation ($F_1$) switchgrass hybrid seeds and plants with superior characteristics.

In another aspect, the variety described herein provides for single or multiple gene converted plants of switchgrass variety EG1102. The transferred gene(s) may be a dominant or recessive allele. In some embodiments, the transferred gene(s) will confer such traits as herbicide resistance, insect resistance, resistance for bacterial, fungal, or viral disease, male fertility, male sterility, male and female sterility, increased biomass yield, drought, increased drought tolerance, increased cold tolerance, increased low light tolerance, modified composition, modified biofuel conversion properties, modified sugar percent, modified lignin content, modified cellulose content, modified hemicellulose content, modified fatty acid metabolism, modified carbohydrate metabolism, modified seed yield, modified protein content, increased nitrogen use efficiency, modified stand establishment, modified flowering time, modified germination rate, modified seed dormancy rate, modified senescence, modified lodging resistance and industrial usage. The gene may be a naturally occurring switchgrass gene or a transgene introduced through genetic engineering techniques.

In another aspect, the variety described herein provides regenerable cells for use in tissue culture of switchgrass plant EG1102. The tissue culture can be capable of regenerating plants having all the physiological and morphological characteristics of the foregoing switchgrass plant, and of regenerating plants having substantially the same genotype as the foregoing switchgrass plant. In some embodiments, the regenerable cells in such tissue cultures will be embryos, protoplasts, meristematic cells, callus, pollen, leaves, anthers, cotyledons, hypocotyl, pistils, roots, root tips, flowers, seeds, petiole, shoots or stems. Still further, the variety described herein provides switchgrass plants regenerated from the tissue cultures of the EG1102.

In addition to the exemplary aspects and embodiments described above, further aspects and embodiments will become apparent by study of the following descriptions.

DEFINITIONS

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Alter. The utilization of up-regulation of a gene, down-regulation of a gene, or gene silencing.

Altered trait. As used herein, "altered trait" means a change in a plant trait such as, but not limited to, herbicide resistance, pest or insect resistance, disease resistance, biomass, sterility or partial sterility, self compatibility, plant metabolism, nitrogen use efficiency, stress tolerance, yield, stand establishment, drought or cold tolerance, flowering time, tolerance to low light, seed dormancy and/or germination, plant growth and/or plant structure, content of cellulose, lignin, hemicellulose, or sugars in plant tissues.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bialaphos herbicide. Bialaphos is a non-selective foliar-applied herbicide and has strong herbicidal activities against a wide range of monocotyledonous and dicotyledonous weeds. Bialaphos, a product of *Streptomyces hygroscopicus*, is a unique tripeptide composed of alanylalanine and phosphinothricin having a C—P—C bond. It is a type of prodrug in which phosphinothricin inhibits glutamine synthetase, accumulates ammonia, and inhibits photosynthesis in plants.

Bialaphos resistance. As used herein, bialaphos resistance also includes tolerance to bialaphos herbicides. Bialaphos resistance is conferred by one or more genes, alleles or events which alter the phosphinothricin acetyl transferase (PAT) enzyme, allowing the enzyme to resist or tolerate the action of bialaphos.

Biomass. Biomass includes harvestable plant tissues such as leaves, stems, and reproductive structures, or all plant tissues such as leaves, stems, roots, and reproductive structures.

Biomass to fuel conversion. The process of deconstructing the three-dimensional plant (biomass) cell wall components to obtain molecules that are fuels or can be made into fuels through chemical, thermochemical or biological processes.

Cell. Cell as used herein includes a plant cell, whether isolated, in tissue culture or incorporated in a plant or plant part.

Coding region/sequence. The region within a DNA molecule (i.e., between the start and stop codons) that encodes the amino acid sequence of a protein.

Cold tolerance. Plant species vary in their capacity to tolerate low temperatures. Chilling-sensitive plant species, including many agronomically important species, can be injured by cold, above-freezing temperatures. At temperatures below the freezing-point of water most plant species will be damaged. Thus, "cold" can be defined as the temperature at which a given plant species will be adversely affected as evidenced by symptoms such as decreased photosynthesis and membrane damage (measured by electrolyte leakage). Since plant species vary in their capacity to tolerate cold, the precise environmental conditions that cause cold stress cannot be generalized. However, cold tolerant plants are characterized by their ability to retain their normal appearance, recover quickly from low temperature conditions, exhibit normal or increased growth under low temperature conditions, and/or have improved cold acclimation. Such cold tolerant plants produce higher biomass and/or yield than plants that are not cold tolerant. Differences in physical appearance, recovery and yield can be quantified and statistically analyzed using well known measurement and analysis methods.

Composition characteristics. The relative concentration of chemical compounds found in biomass feedstock or biomass-derived materials.

Conversion characteristics. The ease with which a biomass feedstock can be broken down into molecules that are valuable fuels (or chemicals) or can be converted into valuable fuels (or chemicals). The desired products can vary. For biological processes, the goal is to maximize yield of monomeric sugars that are released into a liquid phase without further degradation or production of undesirable side products (inhibitors). For thermochemical processes, the goal would be production of liquids or gasses with high energy contents without generating undesirable side products like tars or toxic emissions.

Cotyledon. A cotyledon is a type of seed leaf. The cotyledon contains the food storage tissues of the seed.

Disease resistance. As used herein, the term "disease resistance" is defined as the ability of plants to restrict the activities of a specified pest, such as an insect, fungus, virus, or bacterium.

Disease tolerance. As used herein, the term "disease tolerance" is defined as the ability of plants to endure a specified pest (such as an insect, fungus, virus or bacterium) or an adverse environmental condition and still perform and produce in spite of this disorder.

Drought tolerance. This term refers to the capacity of a plant to minimize the effect of water limitation on growth and development under water deficit conditions. Drought generally refers to water deficit caused by lack of rainfall or limited irrigation. Water deprivation in plants may also be caused by low humidity, high temperatures, saline soils, freezing temperatures or water-logged soils that damage roots and limit water uptake to the shoot. Plants can achieve the maximum growth potential only under an optimal level of available water. Water deficit can cause decreased photosynthesis and cell or plant death in extreme cases and thus a significant reduction in plant productivity (biomass or harvestable yield).

Dry matter yield. The mass of biomass produced (usually reported in T/acre) if the contribution of water is subtracted from the fresh matter weight. Dry matter yield (DMY) yield is calculated using the fresh matter weight (FMW) and a measurement of weight percent moisture (M) in the following equation. DMW=((100−M)/100)*FMY.

Embryo. The embryo is the small plant contained within a mature seed.

Exogenous. With respect to a nucleic acid, this term indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Flowering time/Altered flowering time. Altered flowering time may mean either that: (a) flowering time of a plant is earlier than a wild-type plant (i.e., early flowering) or (b) the flowering time is later than a wild-type plant (i.e. late flowering). Early Flowering: Plant species vary in the temporal lengths of their life cycles. Plants can have life cycles that may be completed within one year or span across several years. Plants generally flower late in their life cycle, after embryogenesis, seedling development and a period of vegetative growth (Walbot (1985) *Trends Genet.* 1:165-169). Flowering time in plants is influenced by many endogenous and environmental factors, including gibberellin biosynthesis and signaling, autonomous controls, light quality and intensity, photoperiod, temperature and availability of nutrients (Garner and Allard (1920) *J. Agric. Res.* 18:553-606; Bernier (1988) *Annu. Rev. Plant Physiol.* 39:175-219; Millar (1999) *New Phytol.* 14:175-197; Battey (2000) *J. Exp. Bot.* 51:1769-1780; Samach and Coupland (2000) *Bioessay,* 22:38-47). Early flowering may mean: (a) that the plant has begun to flower at a time statistically significantly earlier than another plant or plants of a different variety grown under the same conditions because the transition from the vegetative pre-flowering phase to the reproduction phase occurs earlier; or (b) that the plant has begun to flower at a time statistically significantly earlier than another plant or plants of a different variety grown under the same conditions because the growth rate of the plant prior to flowering and/or in the entire life cycle has been enhanced. Early flowering may also be described as a plant flowering at a moment in its life cycle that is at least 1% to 10% earlier in the plant's life cycle compared to another plant or plants of a different variety grown under identical conditions. Alternatively, the plant may begin to flower at a moment in the plant's life cycle that is at least 10% to 25% earlier or at least 25% to 50% earlier or at least 50% to 99% earlier.

Late flowering: In contrast to early flowering, late flowering may mean: (a) that the plant has begun to flower at a time statistically significantly later than another plant or plants of a different variety, grown under the same conditions because the transition from the vegetative, pre-flowering phase to the reproduction phase occurs later; or that the plant has begun to flower at a time statistically significantly later than another plant or plants of a different variety, grown under the same conditions because the growth rate of the plant prior to flowering and/or in the entire life cycle has been decreased. Late flowering can also be described as a plant flowering at a moment in its life cycle that is at least 1% and 10% later in the plant's life cycle compared to a corresponding wild-type plant grown under identical conditions. Alternatively, the plant may begin to flower at a moment in the plant's life cycle that is at least 10% to 25% later or at least 25% to 50% later or at least 50% to 99% later.

Fresh matter yield. The mass of biomass produced (usually reported in T/acre) on an as-received basis, which includes the weight of moisture.

Gene converted (conversion). Gene converted (conversion) plants refers to plants which are developed by a plant breeding technique called backcrossing wherein essentially all of the desired morphological and physiological characteristics of a variety are recovered in addition to the one or more gene(s) transferred into the variety via the backcrossing technique, via genetic engineering or via mutation.

Gene silencing. The interruption or suppression of the expression of a gene at the level of transcription or translation.

Genotype. Refers to the genetic constitution of a cell or organism.

Germination. The emergence and development from the seed embryo of those essential structures of a seedling. Germination is indicative of the ability to produce a normal plant under favorable conditions.

Glyphosate herbicide. As used herein, a glyphosate herbicide is an herbicide that interferes with the enzyme 5-enolpyruvylshikimate-3-phosphate synthase in a plant which eventually results in the death of the plant.

Glyphosate resistance. As used herein, glyphosate resistance also includes tolerance to glyphosate herbicides. Glyphosate resistance is conferred by one or more genes, alleles or events which alter the enzyme 5-enolpyruvylshikimate-3-phosphate synthase allowing the enzyme to resist or tolerate the action of glyphosate herbicides.

Herbicide resistance/tolerance. As used herein, herbicide resistance also includes herbicide tolerance. Herbicide resistance/tolerance is the ability of a plant to survive and reproduce following exposure to a dose of herbicide that would be lethal to a susceptible plant.

Increased biomass. As used herein, increased biomass refers to increased plant height, increased fresh matter yield, increased dry matter yield, and/or increased tiller number.

Linkage. Refers to a phenomenon wherein alleles on the same chromosome tend to segregate together more often than expected by chance if their transmission was independent.

Linkage disequilibrium. Refers to a phenomenon wherein alleles tend to remain together in linkage groups when segregating from parents to offspring, with a greater frequency than expected from their individual frequencies.

Locus. A locus confers one or more traits such as, for example, male sterility, herbicide tolerance, insect resistance, disease resistance, modified fatty acid metabolism, modified carbohydrate metabolism and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Low light tolerance. Low light tolerance refers to the ability of plants to grow and develop under low light quantity that is suboptimal for photosynthesis. Tolerance to light conditions below compensation point, where the compensation point is the amount of light intensity on the light curve where the rate of photosynthesis exactly matches the rate of respiration.

Modified cellulose. Cellulose with an unusual crystalline structure, cellulose deposited in an unusual location in the plant cell wall, or cellulose present in concentrations higher or lower than normally seen.

Modified hemicellulose. Hemicellulose with an unusual branching structure, hemicellulose deposited in an unusual location in the plant cell wall, or hemicellulose present in concentrations higher or lower than normally seen.

Modified lignin. Lignin with an unusual branching structure, lignin deposited in an unusual location in the plant cell wall, lignin with an unusual proportion of syringial, guaiacyl or p-hydroxyphenyl aromatic groups, or lignin present in concentrations that are higher or lower than normally seen.

Modified sugars. Modified cellulose, modified hemicellulose or sucrose present in concentrations that are higher or lower than normally seen.

Mutagen. As used herein, a mutagen is a physical or chemical agent that changes the genetic information of a plant and thus increases the frequency of mutations above the natural background level. Examples of mutagens include but are not limited to ionizing radiation such as ultraviolet light, gamma rays and alpha particles; base analogs; deaminating agents such as nitrous acid; intercalating agents such as ethidium bromide; alkylating agents such as bromouracil; transposons; some natural plant alkaloids, such as those from Vinca species; certain chemicals such as bromine and sodium azide; and Psoralen combined with ultraviolet radiation.

Nitrogen use efficiency. Nitrogen use efficiency refers to the amount of grain yield or biomass relative to amount of N input.

Operably linked. As used herein, "operably linked" means there is a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Partial sterility. Not producing or incapable of producing offspring at a level that is comparable to the wild type. Not producing or incapable of producing seed, fruit spores, or other reproductive structures at a level that is comparable to the wild type.

Pedigree distance. Relationship among generations based on their ancestral links as evidenced in pedigrees. May be measured by the distance of the pedigree from a given starting point in the ancestry.

Percent identity. Percent identity as used herein refers to the comparison of the homozygous alleles of two switchgrass varieties. Percent identity is determined by comparing a statistically significant number of the homozygous alleles of two developed varieties. For example, a percent identity of 90% between switchgrass variety 1 and switchgrass variety 2 means that the two varieties have the same allele at 90% of their loci.

Percent similarity. Percent similarity as used herein refers to the comparison of the homozygous alleles of a switchgrass variety such as EG1102 with another plant, and if the homozygous allele of EG1102 matches at least one of the alleles from the other plant then they are scored as similar. Percent similarity is determined by comparing a statistically significant number of loci and recording the number of loci with similar alleles as a percentage. A percent similarity of 90% between EG1102 and another plant means that EG1102 matches at least one of the alleles of the other plant at 90% of the loci.

Pest resistance. As used herein, the term "pest resistance" is defined as the ability of plants to restrict the activities of a specified pest, such as an insect or nematode.

Pest tolerance. As used herein, the term "pest tolerance" is defined as the ability of plants to endure a specified pest (such as an insect or a nematode) still perform and produce in spite of this disorder.

Plant. As used herein, the term "plant" includes reference to an immature or mature whole plant, including a plant from which seed or anthers have been removed. A seed or embryo that will produce the plant is also considered to be the plant.

Plant characteristic. A plant characteristic can be a morphological, physiological, agronomic, or genetic feature of a plant.

Plant growth. This term refers to the process by which plants increase in size and mass. The increase in the number and size of plant organs is directly associated with an increase in cell numbers and cell size, which involves cell division, growth, expansion and differentiation. Plants utilize sunlight, water, carbon dioxide and minerals in biosynthesis to provide energy and substances required for growth. Plant growth can be generally divided into vegetative and reproductive growth in the life cycle.

Plant height. Plant height is taken from the top of the soil to the top node of the plant and is measured in centimeters.

Plant metabolism. The biological process of converting nutrients in the air, water and soil into plant biomass during growth, development or repair.

Plant parts. As used herein, the term "plant parts" (or a switchgrass plant, or a part thereof) includes protoplasts, leaves, stems, roots, root tips, anthers, pistils, seed, embryo, pollen, ovules, cotyledon, hypocotyl, flower, shoot, tissue, petiole, cells, meristematic cells and the like.

Plant structure. As used herein, the term "plant structure" includes plant stature, plant habit, plant anatomy (e.g., stem anatomy), and/or plant architecture.

Progeny. The term includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

Quantitative trait loci (QTL). Quantitative trait loci (QTL) refer to genetic loci that control to some degree numerically representable traits that are usually continuously distributed.

Regeneration. As used herein, regeneration refers to the development of a plant from tissue culture.

Regulatory region/sequence. As used herein, regulatory region or sequence refers to a DNA sequence involved in regulating the expression of a gene, e.g., a promoter or operator region (in the DNA molecule).

Seed dormancy. A state in which seeds are prevented from germination even when environmental conditions are favorable.

Self-compatibility. Capable of effective self-pollination that results in the production of seeds and fruits.

Stand establishment. Stand establishment refers to the survivability and density of areas of land newly planted with switchgrass, typically by seed or stem propagation.

Sterility. Not producing or incapable of producing offspring. Not producing or incapable of producing seed, fruit spores, or other reproductive structures.

Stress tolerance. The ability to prevent, decrease, or repair the injury induced by an abiotic or biotic stress on a plant or plant population.

Switchgrass population. A group of switchgrass plants, the majority of which share one or more characteristics.

Synthetic population. A synthetic population is group of switchgrass plants, the majority of which share one or more characteristics, that is prepared by intercrossing selected clones or inbred lines.

Tiller. As used herein, tiller means the stem of the switchgrass plant.

Wild type. A naturally occurring switchgrass plant that has not undergone crop selection or breeding.

Yield. This term means a quantity of plant material, typically biomass, fruit or seeds, harvested per unit area of land.

DETAILED DESCRIPTION OF THE INVENTION

A novel switchgrass variety, hereafter designated as EG1102 is described herein, including seeds, plants, and plant parts. The new variety has increased biomass, increased disease resistance and increased spring re-growth in comparison to Kanlow, the switchgrass ecotype from which it was bred. Increased biomass can be, for example, increased plant height, increased fresh matter yield, increased dry matter yield, or increased tiller number. Described herein are methods for producing a switchgrass plant by crossing a first parent switchgrass plant with a second parent switchgrass plant, wherein the first or second switchgrass plant is the switchgrass plant from variety EG1102. Further, both first and second parent switchgrass plants may be from variety EG1102. Therefore, any methods using switchgrass variety EG1102 are envisioned: selfing, backcrosses, hybrid breeding, and crosses to populations. Any plants or synthetic populations produced using switchgrass variety EG1102 as at least one parent are within the scope of the variety and methods described herein.

Additional methods for using EG1102 to develop novel varieties include, but are not limited to, expression vectors introduced into plant tissues using a direct gene transfer method such as microprojectile-mediated delivery, DNA injection, electroporation and the like. Expression vectors can also be introduced into plant tissues by using either microprojectile-mediated delivery with a biolistic device or by using *Agrobacterium*-mediated transformation. Transformant plants obtained with the protoplasm of EG1102 are intended to be within the scope of the variety and methods described herein.

I. VARIETY DESCRIPTION INFORMATION

Cultivar EG1102 is an open-pollinated switchgrass cultivar developed through a complex selection and breeding program. The program began by space planting 1000 genotypes from switchgrass Kanlow in a honeycomb design in a field near Athens, Ga., U.S.A. This design was chosen because of its ability to remove micro-environment variation during assessment of individual, un-replicated genotypes. Based on phenotypic selection for plant biomass yield, the best potential genotypes were then identified and heritability estimates were found to be adequate to incur good gains from selection and genotypes were then identified from each cultivar which had excellent performance. Cuttings of each of these superior genotypes were clonally multiplied in the greenhouse and used in a polycrossing program to produce half-sib progeny of each and to assess their seed yield. The half-sib progeny were then space planted in the sward plots over locations and years and 5 highest seed yielding families and the 5 best genotypes within those families were identified and selected. The 25 genotypes were then clonally replicated, inter-mated in replicated polycross nursery, and equal amounts of seed bulked across reps for each genotype to produce the Syn 1 seed (pre-breeder seed) of EG1102 in isolation near Athens, Ga. Syn 2 seed was produced by increasing the Syn 1 seed in isolation near Ardmore, Okla. No variants were observed for ploidy levels or lodging, and no off-types were observed when examined for two synthetic generations (Syn 1 vs. Syn 2) in Athens, Ga. and Ardmore, Okla.

EG1102 is expected to have some off types. However, the cultivar is uniform for most of phenotypic traits. Since switchgrass variety EG1102 is homogeneous, it can be reproduced by planting seeds of such cultivar, growing the resulting switchgrass plant under sib-pollinating conditions with adequate population isolation, and harvesting the resulting seed using agronomic practices.

For the characteristics in Table 1, a total of 90 spaced plants were grown in 2 locations, Ardmore, Okla. and College Station, Tex. The experimental design was a RCBD with six replications; one plot consisted of 15 spaced plants, row spacing was 152 cm, and plants were spaced 76 cm within a row. Individual seedlings were started in a greenhouse using SC-9 Cone-tainers™ (Stuewe and Sons, Corvalis, Oreg.) in March, 2008 at both locations. Single plants were transplanted in Ardmore, Okla. on May 23, 2008, and Jun. 25, 2008 in College Station, Tex. At both locations 50 lbs/N/A were applied at planting and transplants were irrigated for establishment. Plant characteristics were measured at the end of the growing season on mature plants. A total of 180 data points were measured.

For seed characteristics seed was hand harvested from 3 panicles from each plant and bulked per plot, measurements were taken from 100 seeds from 3 replications from each location, i.e. a total of 600 seeds were measured for seed characteristics.

The following traits have been repeatedly observed and are determined to be the unique characteristics of EG1102.

TABLE 1

VARIETY DESCRIPTION INFORMATION

PLANT:

Species: *Panicum virgatum*
Ploidy: Tetraploid
Area of adaptation: Adapted to USDA Hardiness Zones 6-9
Plant height: 161 cm; 0.7 cm shorter than Alamo; 13.0 cm taller than Kanlow
Growth habit score: 4.5 where 1 = Prostrate and 9 = Upright
Heading: Medium; 2 days earlier than Alamo; 2 days later than Kanlow

TABLE 1-continued

VARIETY DESCRIPTION INFORMATION

LEAVES:

Flag leaf blade length (after anthesis): 40.9 cm; 0.9 cm longer than Alamo
Flag leaf blade width: 1.24 cm; 0.04 cm wider than Alamo
Sheath length of flag leaf (Flag leaf collar to subtending node): 13.1 cm; 0.1 cm longer than Kanlow

SEED:

Panicle length: 42.3 cm; 0.7 cm shorter than Alamo; 6.1 cm longer than Kanlow
Mg/1000 seeds: 1.342
Total length of 30 seeds: 0.252 cm
Total width of 30 seeds: 0.105 cm

DISEASE REACTION:

Rust (*Puccinia* spp.): Moderately resistant

PHYSIOLOGICAL CHARACTERISTICS:

Percent lignin: 18.1
Percent protein: 2.3
Percent ash: 5.3
Percent extractives: 12.6
Percent glucan: 31.7
Percent xylan: 21.2
Percent sucrose: 1.3

These characteristics and others described herein distinguish EG1102 as a new and distinct cultivar of *Panicum*.

II. GENETIC MARKER PROFILE OF EG1102

In addition to phenotypic observations, a plant can also be identified by its genotype. The genotype of a plant can be characterized through a genetic marker profile which can identify plants of the same variety or a related variety or be used to determine or validate a pedigree. Means of performing genetic marker profiles using genetic polymorphisms are well known in the art. For example, genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et. al, "An Integrated Genetic Linkage Map of the Soybean Genome" *Crop Science* 39:1464-1490 (1999), and Berry et al., "Assessing Probability of Ancestry Using Simple Sequence Repeat Profiles: Applications to Maize Inbred Lines and Soybean Varieties" *Genetics* 165:331-342 (2003), each of which are incorporated by reference for this purpose.

Particular markers used for these purposes are not limited to any particular set of markers, but are envisioned to include any type of marker and marker profile which provides a means of distinguishing varieties. For example, genetic polymorphisms can be discrete allelic sequence differences in a population. Typically, an allele that is present at 1% or greater is considered to be a genetic polymorphism.

In addition to being used for identification of switchgrass variety EG1102 and plant parts and plant cells of variety EG1102, the genetic profile may be used to identify a switchgrass plant produced through the use of EG1102 or to verify a pedigree for progeny plants produced through the use of EG1102. The genetic marker profile is also useful in breeding and developing backcross conversions.

EG1102 comprises a switchgrass plant or population of plants characterized by molecular and physiological data obtained from the representative sample of said variety deposited with the American Type Culture Collection (ATCC). EG1102 can also be a switchgrass plant formed by the combination of the disclosed switchgrass plant or plant cell with another switchgrass plant or cell and comprising the alleles, combination of alleles, or allele frequencies of the variety.

In addition, plants and plant parts substantially benefiting from the use of EG1102 in their development, such as EG1102 comprising a backcross conversion, transgene, or genetic sterility factor, may be identified by having a molecular marker profile with a high percent identity to EG1102. Such a percent identity might be 95%, 96%, 97%, 98%, 99%, 99.5% or 99.9% identical to EG1102.

The genetic marker profile of EG1102 also can be used to identify essentially derived varieties and other progeny varieties developed from the use of EG1102, as well as cells and other plant parts thereof. Progeny plants and plant parts produced using EG1102 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from switchgrass variety EG1102, as measured by either percent identity or percent similarity. Such progeny may be further characterized as being within a pedigree distance of EG1102, such as within 1, 2, 3, 4 or 5 or less cross-pollinations to a switchgrass plant other than EG1102 or a plant that has EG1102 as a progenitor. Unique molecular profiles may be identified with other molecular tools such as microsatellites or SNPs. Markers can be used to map QTLs that can also be used to distinguish EG1102 or identify its potential progeny.

While determining the genetic marker profile of the plants described supra, a large number of SNIPs were examined and about 18 unique markers were identified which did not appear in either parent of the present invention, EG1102. Such unique profiles may arise during the breeding process from recombination or mutation. A combination of several unique alleles provides a means of identifying a plant variety, an $F_1$ progeny produced from such variety, and progeny produced from such variety.

III. TISSUE CULTURE

Further reproduction of the variety can occur by tissue culture and regeneration. Thus, another aspect of the methods and variety described herein is to provide cells which upon growth and differentiation produce switchgrass plants having the characteristics of switchgrass variety EG1102. As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, petioles, leaves, stems, shoots, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference for this purpose. Examples of methods of tissue culture that can be used with switchgrass include, but are not limited to, switchgrass callus culture (Gupta and Cogner, 1999, "Somatic Embryogenesis and Plant Regeneration from Suspension Cultures of Switchgrass" *Crop Sci* 39:243-247; Denchev and Conger, 1994 "Plant Regeneraton from Callus Cultures of Switchgrass" *Crop Sci* 34:1623-1627) and switchgrass stem node culture propagation (Alexandrova et al. 1996 "Micropropagation of Switchgrass by Node Culture" *Crop Sci* 36:1709-1711), or variations thereof, the disclosures of which are incorporated herein by reference for this purpose.

IV. SWITCHGRASS BREEDING

In one aspect, the methods and variety described herein includes the use of EG1102 plants in methods of breeding switchgrass. There are two different general switchgrass ecotypes, lowland and upland. Lowland switchgrass are predominantly tetraploid (2n=4x=36 chromosomes) while upland switchgrass cultivars are predominantly octaploid (2n=8x=72 chromosomes). Switchgrass variety EG1102 is a lowland ecotype. Thus, plants of EG1102 can be intercrossed with other lines or varieties that are also of the lowland ecotype, as well as plants of the upland ecotype that have the same ploidy level.

Using EG1102 to Develop Other Switchgrass Varieties

Switchgrass varieties such as EG1102 are typically developed for use as forage, grazing for livestock, as erosion control and as biofuel. However, switchgrass varieties such as EG1102 also provide a source of breeding material that may be used to develop new switchgrass varieties. Plant breeding techniques known in the art and used in a switchgrass plant breeding program include, but are not limited to, recurrent selection, mass selection, bulk selection, backcrossing, pedigree breeding, open pollination breeding, restriction fragment length polymorphism enhanced selection, genetic marker enhanced selection, making double haploids, selfing, sibling crosses, backcrosses, hybrid production, mutation breeding, crosses to populations and transformation. Often combinations of these techniques are used. The development of switchgrass varieties in a plant breeding program requires, in general, the development and evaluation of plant populations. There are many analytical methods available to evaluate a new variety. The oldest and most traditional method of analysis is the observation of phenotypic traits but genotypic analysis may also be used. For example, one of skill in the art may use switchgrass variety EG1102 in selection and breeding methods to produce plants having altered disease resistance, pest resistance, plant metabolism, herbicide resistance, yield, plant growth and/or plant structure, sterility, biomass, stand establishment, drought or cold tolerance, flowering time, after-harvest recovery rate, stress tolerance, tolerance to low light, nitrogen use efficiency, seed dormancy and/or germination, the percentages of sugars, the percent of lignin, the percent of cellulose and/or hemicellulose, and the biomass to fuel conversion properties of switchgrass.

Breeding Methods

Described herein are methods for producing a switchgrass plant by crossing a first parent switchgrass plant with a second parent switchgrass plant wherein either the first or second parent switchgrass plant is variety EG1102. The other parent may be any other switchgrass plant, such as a switchgrass plant that is part of a synthetic or natural population. Any such methods using switchgrass variety EG1102 are envisioned. These methods are well known in the art and some of the more commonly used breeding methods are described below. Descriptions of breeding methods can be found in one of several reference books (e.g., Allard, *Principles of Plant Breeding*, 1960; Simmonds, *Principles of Crop Improvement*, 1979; Sneep et al., 1979 *Plant Breeding Perspectives*; Fehr, 1991 *Principles of Cultivar Development—Theory and Technique*).

The following describes breeding methods that may be used with switchgrass variety EG1102 in the development of further switchgrass plants. One such embodiment is a method for developing a cultivar EG1102 progeny switchgrass plant in a switchgrass plant breeding program comprising: obtaining the switchgrass plant, or a part thereof, of cultivar EG1102 utilizing said plant or plant part as a source of breeding material and selecting a switchgrass cultivar EG1102 progeny plant with molecular markers in common with variety EG1102 and/or with morphological and/or physiological characteristics described herein.

Another method involves producing a population of switchgrass variety EG1102 progeny switchgrass plants, comprising crossing cultivar EG1102 with another switchgrass plant, thereby producing a population of switchgrass plants, which, on average, derive 50% of their alleles from switchgrass variety EG1102. A plant of this population may be selected and repeatedly selfed or sibbed with a switchgrass cultivar resulting from these successive filial generations. In some embodiments, the switchgrass cultivar produced by this method and that has obtained at least 50% of its alleles from switchgrass variety EG1102.

One of ordinary skill in the art of plant breeding would know how to evaluate the traits of two plant varieties to determine if there is no significant difference between the two traits expressed by those varieties. For example, see Fehr and Walt, *Principles of Cultivar Development*, p 261-286 (1987). Thus the methods and variety described herein includes switchgrass cultivar EG1102 progeny switchgrass plants comprising a combination of at least two cultivar EG1102 traits selected from the group consisting of those listed in Tables 1-4 or the cultivar EG1102 combination of traits listed in the Summary of the Invention, so that said progeny switchgrass plant is not significantly different for said traits than switchgrass variety EG1102 as determined at the 5% significance level when grown in the same environmental conditions. Using techniques described herein, molecular markers may be used to identify said progeny plant as a switchgrass variety EG1102 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of switchgrass variety EG1102 may also be characterized through their filial relationship with switchgrass variety EG1102, as for example, being within a certain number of breeding crosses of switchgrass variety EG1102. A breeding cross is a cross made to introduce new genetics into the progeny, and is distinguished from a cross, such as a self or a sib cross, made to select among existing genetic alleles. The lower the number of breeding crosses in the pedigree, the closer the relationship between switchgrass variety EG1102 and its progeny. For example, progeny produced by the methods described herein may be within 1, 2, 3, 4 or 5 breeding crosses of switchgrass variety EG1102.

As used herein, the term "plant" includes plant cells, plant protoplasts, plant cell tissue cultures from which switchgrass plants can be regenerated, plant calli, plant clumps, and plant cells that are intact in plants or parts of plants, such as embryos, pollen, ovules, flowers, leaves, roots, root tips, anthers, pistils, cotyledons, hypocotyls, meristematic cells, stems, shoots, pistils, petiole, and the like.

Recurrent Selection and Mass Selection

Recurrent selection is a method used in a plant breeding program to improve a population of plants. EG1102 is suitable for use in a recurrent selection program. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties. The number of parental plant varieties, populations, wild accessions, ecotypes, etc., that are used to generate a synthetic can vary from as little as 10 to as much as 500. Typically, about 100 to 300 varieties, populations, etc., are used a parents for the synthetic variety. Seed from the parental seed production plot of a synthetic variety can be sold to the farmer. Alternatively, seed from the parental seed production plot can subsequently undergo one or two generations of multiplication, depending on the amount of seed produced in the parental plot and the demand for seed.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Breeding of Open-Pollinated Populations

EG1102 can be used as a parent to develop improved open-pollinated populations of switchgrass. Such plant breeding procedures for improving open-pollinated populations are well known in the art. Detailed breeding methodologies specifically applicable to switchgrass are provided in Bouton, "Molecular Breeding of Switchgrass for Use as a Biofuel Crop" *Current Opinions in Genetics & Development*, 2007; Missaoui et al., "The Effect of Low Plant Density on Response to Selection for Biomass Production in Switchgrass" *Euphytica* 2005; and Burns et al. "Registration of 'BoMaster' Switchgrass" *J. Plant Reg* 2:31-32, 2008. Use of EG1102 to develop an improved open-pollinated population can utilize a program of, for example, mass selection, selection with progeny testing, or using EG1102 can be used as a parent to generate a synthetic variety. A synthetic variety is produced by crossing several parental plants.

Mutation Breeding

Mutation breeding is another method of introducing new traits into switchgrass variety EG1102. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (such as from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, 1993. *Principles of Cultivar Development*, Macmillan Publishing Company. In addition, mutations created in other switchgrass plants may be used to produce a backcross conversion of switchgrass variety EG1102 that comprises such mutation.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing switchgrass variety EG1102.

Isozyme Electrophoresis and RFLPs have been widely used to determine genetic composition. Shoemaker and Olsen, (O'Brien, S. J., (ed.) 1993. *Genetic Maps: Locus Maps of Complex Genomes*. Cold Spring Harbor Laboratory Press. Cold Spring Harbor, N.Y.), developed a molecular genetic linkage map that consisted of 25 linkage groups with about 365 RFLP, 11 RAPD (random amplified polymorphic DNA), three classical markers, and four isozyme loci. See also, Shoemaker R. C. 1994. "RFLP Map of Soybean" p 299-309 In R. L. Phillips and I. K. Vasil (ed.) *DNA-Based Markers in Plants*. Kluwer Academic Press Dordrecht, the Netherlands. In switchgrass, Missaoui also described RFLP markers (Missaoui et al., 2006, "Molecular markers for the classification of switchgrass (*Panicum virgatum* L.) germplasm and to assess genetic diversity in three synthetic switchgrass populations" *Genetic Resources and Crop Evolution* 53:1291-1302).

SSR technology is currently the most efficient and practical marker technology; more marker loci can be routinely used and more alleles per marker locus can be found using SSRs in comparison to RFLPs. For example Diwan and Cregan, described a highly polymorphic microsatellite loci in soybean with as many as 26 alleles. (Diwan, N., and P. B. Cregan. 1997 "Automated sizing of fluorescent-labeled simple sequence repeat (SSR) markers to assay genetic variation in soybean". *Theor. Appl. Genet.* 95:220-225). Single Nucleotide Polymorphisms (SNPs) may also be used to identify the unique genetic composition of EG1102 and progeny varieties retaining that unique genetic composition. Various molecular marker techniques may be used in combination to enhance overall resolution.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Genomic Selection

One potential problem with marker assisted selection is that only a limited proportion of the total genetic variance is captured by the markers. An alternative to tracing a limited number of QTL with markers is to trace all the QTL. This can be done by dividing the entire genome up into chromosome segments, for example defined by adjacent markers, and then tracing all the chromosome segments. This method was termed genomic selection by Meuwissen et al. 2001. "Prediction of total genetic value using genome-wide dense marker maps" *Genetics* 157:1819-1829. With the availability of high-density marker maps and cost effective genotyping, genomic selection methods may provide faster genetic gain than can be achieved by current selection methods based on phenotypes and pedigree. Some of the factors driving the accuracy of genomic selection include marker density and marker type (i.e., microsatellite and SNP markers). Genomic selection exploits linkage disequilibrium (LD)—the assumption is that the effects of the chromosome segments will be the same across the population because the markers are in LD with the QTL that they bracket. With genomic selection, selection is typically on the sum of estimates of effects of all marker intervals across the genome, fitted either as fixed (fixed GS) or random (random GS) effects. Responses to selection are tracked by indices over generations. The efficiency of genomic selection over standard marker assisted selection depends on stringency of the threshold used for QTL detection. One skilled in the art will be able to optimize these factors that affect genomic selection for a particular species such as switchgrass.

Production of Double Haploids

The production of double haploids can also be used for the development of plants with a homozygous phenotype in the breeding program. For example, a switchgrass plant for which switchgrass cultivar EG1102 is a parent can be used to produce double haploid plants. Double haploids are produced by the doubling of a set of chromosomes (1 N) from a heterozygous plant to produce a completely homozygous individual. For example, see Wan et al., "Efficient Production of Doubled Haploid Plants Through Colchicine Treatment of Anther-Derived Maize Callus", *Theor. App. Genet.* 77:889-892, 1989 and U.S. Pat. No. 7,135,615. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6 (Coe, 1959, *Am. Nat.* 93:381-382; Sharkar and Coe, 1966, *Genetics* 54:453-464), KEMS (Deimling, Roeber, and Geiger, 1997, *Vortr. Pflanzenzuchtg* 38:203-224), or KMS and ZMS (Chalyk, Bylich & Chebotar, 1994, *MNL* 68:47; Chalyk & Chebotar, 2000, *Plant Breeding* 119:363-364), and indeterminate gametophyte (ig) mutation (Kermicle 1969 *Science* 166:1422-1424).

Methods for obtaining haploid plants are also disclosed in Kobayashi, M. et al., *J. Heredity* 71(1):9-14, 1980, Pollacsek, M., *Agronomie* (Paris) 12(3):247-251, 1992; Cho-Un-Haing et al., *J. Plant Biol.*, 1996, 39(3):185-188; Verdoodt, L., et al., February 1998, 96(2):294-300; "Genetic Manipulation in Plant Breeding", *Proceedings International Symposium Organized by EUCARPIA*, Sep. 8-13, 1985, Berlin, Germany; Chalyk et al., 1994, *Maize Genet Coop. Newsletter* 68:47.

Thus, one embodiment is a process for making a substantially homozygous EG1102 progeny plant by producing or obtaining a seed from the cross of EG1102 and another switchgrass plant and applying double haploid methods to the $F_1$ seed or $F_1$ plant or to any successive filial generation. Based on studies in maize and more recently in switchgrass, such methods would decrease the number of generations required to produce a variety with similar genetics or characteristics to EG1102. See Bernardo, R. and Kahler, A. L., *Theor. Appl. Genet.* 102:986-992, 2001.

In particular, a process of making seed retaining a molecular marker profile of switchgrass variety EG1102 is contemplated, such process comprising obtaining or producing $F_1$ seed for which switchgrass variety EG1102 is a parent, inducing doubled haploids to create progeny without the occurrence of meiotic segregation, obtaining a molecular marker profile of switchgrass variety EG1102, and selecting progeny that retain a molecular marker profile of EG1102.

Descriptions of other breeding methods that are commonly used for different traits and crops can be found in one of several reference books (e.g., Allard, 1960; Simmonds, 1979; Sneep et al., 1979; Fehr, 1987).

Gene Conversions

When the term "switchgrass plant" is used in the context of the methods and varieties described herein, this also includes any gene conversions of that variety. The term gene converted plant as used herein refers to those switchgrass plants which are developed by a plant breeding technique called backcrossing wherein essentially all of the desired morphological and physiological characteristics of a variety are recovered in addition to the one or more genes transferred into the variety via the backcrossing technique. Backcrossing methods can be used with the methods and variety described herein to improve or introduce one or more characteristics into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental switchgrass plant that contributes the gene(s) for the desired characteristic is termed the nonrecurrent or donor parent. This terminology refers to the fact that the nonrecurrent parent is used one time in the backcross protocol and therefore does not recur. The parental switchgrass plant to which the gene or genes from the nonrecurrent parent are transferred is known as the recurrent parent as it is used for several rounds in the backcrossing protocol (Poehlman & Sleper, 1994; Fehr, *Principles of Cultivar Development* pp. 261-286 (1987)). In a typical backcross protocol, the original variety of interest (recurrent parent) is crossed to a second variety (nonrecurrent parent) that carries the gene(s) of interest to be transferred. The resulting progeny from this cross are then crossed again to the recurrent parent and the process is repeated until a switchgrass plant is obtained wherein essentially all of the desired morphological and physiological characteristics of the recurrent parent are recovered in the converted plant, in addition to the transferred gene(s) from the nonrecurrent parent.

The selection of a suitable recurrent parent is an important step for a successful backcrossing procedure. The goal of a backcross protocol is to alter or substitute one or more traits or characteristics in the original variety. To accomplish this, one or more genes of the recurrent variety is/are modified or substituted with the desired gene(s) from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some agronomically important trait to the plant. The exact backcrossing protocol will depend on the characteristic(s) or trait(s) being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic(s) has been successfully transferred.

Many traits have been identified that are not regularly selected for in the development of a new variety but that can be improved by backcrossing techniques. Traits may or may not be transgenic; examples of these traits include but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus. Several of these traits are described in U.S. Pat. Nos. 5,959,185; 5,973,234 and 5,977,445; the disclosures of which are specifically hereby incorporated by reference for this purpose.

Introduction of a New Trait or Locus into EG1102

Variety EG1102 represents a new base genetic variety into which a new locus or trait may be introgressed. Direct transformation and backcrossing represent two important methods that can be used to accomplish such an introgression. The term backcross conversion and locus conversion are used interchangeably to designate the product of a backcrossing program.

Backcross Conversions of EG1102

A backcross conversion of EG1102 occurs when DNA sequences are introduced through backcrossing (Poehlman, *Breeding Field Crops*, p. 204 (1987), with EG1102 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., "Marker-assisted Selection in Backcross Breeding" In: *Proceedings Symposium of the Analysis of Molecular Data*, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes vs. unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Hallauer et al. in *Corn and Corn Improvement*, Sprague and Dudley, Third Ed. 1998). Desired traits that may be transferred through backcross conversion include, but are not limited to, sterility (nuclear and cytoplasmic), fertility restoration, nutritional enhancements, drought tolerance, nitrogen utilization, altered fatty acid profile, altered carbohydrate profile, industrial enhancements, disease resistance (bacterial, fungal or viral), insect resistance and herbicide resistance. In addition, an introgression site itself, such as an FRT site, Lox site or other site-specific integration site, may be inserted by backcrossing and utilized for direct insertion of one or more genes of interest into a specific plant variety. In some embodiments, the number of loci that may be backcrossed into EG1102 is at least 1, 2, 3, 4, or 5 and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of a site-specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, *Breeding Field Crops*, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant and easily recognized traits.

One process for adding or modifying a trait or locus in switchgrass variety EG1102 comprises crossing EG1102 plants grown from EG1102 seed with plants of another switchgrass variety that comprise the desired trait or locus, selecting $F_1$ progeny plants that comprise the desired trait or locus to produce selected $F_1$ progeny plants, crossing the selected progeny plants with the EG1102 plants to produce backcross progeny plants, selecting for backcross progeny plants that have the desired trait or locus and the morphological characteristics of switchgrass variety EG1102 to produce selected backcross progeny plants; and backcrossing to EG1102 three or more times in succession to produce selected fourth or higher backcross progeny plants that comprise said trait or locus. The modified EG1102 may be further characterized as having the physiological and morphological characteristics of switchgrass variety EG1102 listed in Tables 1-4 and/or may be characterized by percent similarity or identity to EG1102 as determined by SSR markers. The above method may be utilized with fewer backcrosses in appropriate situations, such as when the donor parent is highly related or markers are used in the selection step. Desired traits that may be used include those nucleic acids known in the art, some of which are mentioned herein, that will affect traits through nucleic acid expression or inhibition. Desired loci include the introgression of FRT, Lox and other sites for site specific integration, which may also affect a desired trait if a functional nucleic acid is inserted at the integration site.

Pedigree Breeding

Pedigree breeding starts with the crossing of two genotypes, such as EG1102 and another switchgrass variety having one or more desirable characteristics that is lacking or which complements EG1102. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. In some embodiments, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a switchgrass variety may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the non-recurrent parent. This approach leverages the value and strengths of the recurrent parent for use in new switchgrass varieties.

Therefore, an embodiment is a method of making a backcross conversion of switchgrass variety EG1102, comprising the steps of crossing a plant of switchgrass variety EG1102 with a donor plant comprising a desired trait, selecting an $F_1$ progeny plant comprising the desired trait, and backcrossing the selected $F_1$ progeny plant to a plant of switchgrass variety EG1102. This method may further comprise the step of obtaining a molecular marker profile of switchgrass variety EG1102 and using the molecular marker profile to select for a progeny plant with the desired trait and the molecular marker profile of EG1102. In one embodiment the desired trait is a mutant gene or transgene present in the donor parent.

In addition, the above process and other similar processes described herein may be used to produce first generation progeny switchgrass seed by adding a step at the end of the process that comprises crossing EG1102 with the introgressed trait or locus with a different switchgrass plant and harvesting the resultant first generation progeny switchgrass seed.

V. TRANSGENIC SWITCHGRASS

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are inserted into the genome using transformation are referred to herein collectively as "transgenes". In some embodiments, a transgenic variant of EG1102 may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the methods and variety described herein also relates to transgenic variants of the claimed switchgrass variety EG1102.

One embodiment is a process for producing switchgrass variety EG1102 further comprising a desired trait, said process comprising transforming a switchgrass plant of variety EG1102 with a transgene that confers a desired trait. Another embodiment is the product produced by this process. In one embodiment the desired trait may be one or more of herbicide resistance, insect resistance, disease resistance, or modified fatty acid or carbohydrate metabolism.

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119. Transformation methods well known in the art include, but are not limited to, *Agrobacterium*-mediated transformation, direct gene transfer methods, sonication of target cells, direct uptake of DNA into protoplasts using $CaCl_2$ precipitation or polyvinyl alcohol or poly-L-ornithine, or electroporation of protoplasts and whole cells and tissues.

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

Commonly used selectable marker genes for plant transformation include, but are not limited to, neomycin phosphotransferase II (nptII), hygromycin phosphotransferase, gentamycin acetyl transferase, streptomycin phosphotransferase and aminoglycoside-3'-adenyl transferase, the bleomycin resistance determinant, glyphosate resistance genes, glufosinate resistance genes, or bromoxynil resistance genes. Other selectable marker genes for plant transformation include, for example, mouse dihydrofolate reductase, plant 5-enolpyruvylshikimate-3-phosphate synthase, plant acetolactate synthase, β-glucuronidase (GUS), β-galactosidase, chloramphenicol acetyltransferase, Green Fluorescent Protein, and luciferase.

Several types of promoters are well known in the transformation arts as are other regulatory elements that can be used alone or in combination with promoters. As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner. Some suitable regulatory regions initiate transcription only, or predominantly, in certain cell types. Methods for identifying and characterizing regulatory regions in plant genomic DNA are known, including, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996). Examples of various regulatory regions are described in more detail in U.S. Patent Application Ser. Nos. US20080072340, US20080044898, US20070277269, US20070226830, US20070136839, US 20070124834, and US 20060107346. It will be appreciated that a regulatory region may meet criteria for one classification based on its activity in one plant species, and yet meet criteria for a different classification based on its activity in another plant species. Examples of regulatory regions include broadly expressing promoters, root promoters, maturing endosperm promoters, ovary tissue promoters, embryo sac/early endosperm promoters, embryo promoters, photosynthetic tissue promoters, vascular tissue promoters, inducible promoters, basal promoters, or other regulatory regions.

With transgenic plants according to the methods and variety described herein, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a one embodiment, the transgenic plant provided for commercial production of foreign protein is a switchgrass plant. In another embodiment, the biomass of interest is leaves, stems, or other plant parts. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant.

Wang et al. discuss "Large Scale Identification, Mapping and Genotyping of Single-Nucleotide Polymorphisms in the Human Genome", *Science,* 280:1077-1082, 1998, and similar capabilities are becoming increasingly available for the switchgrass genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant and/or population. Map comparisons would involve hybridizations, RFLP, PCR, SSR and sequencing, all of which are conventional techniques. SNPs may also be used alone or in combination with other techniques.

Likewise, by means of the methods and variety described herein, plants can be genetically engineered to express various phenotypes of agronomic interest. Through the transformation of switchgrass the expression of genes can be altered to enhance disease resistance, insect resistance, herbicide resistance, agronomic, seed quality and other traits. Transformation can also be used to insert DNA sequences which control or help control male-sterility. DNA sequences native to switchgrass as well as non-native DNA sequences can be transformed into switchgrass and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants. Many techniques for gene silencing are well known to one of skill in the art.

Likewise, by means of the methods and variety described herein, agronomic genes can be expressed in transformed plants. More particularly, plants can be genetically engineered to express various phenotypes of agronomic interest. Examples of type of useful genes that can be transformed into switchgrass EG1102 include, but are not limited to, plant disease resistance genes, pest resistance genes, a *Bacillus thuringiensis* protein a derivative thereof or a synthetic polypeptide modeled thereon, an enzyme inhibitor, an enzyme that modulate plant metabolism, a toxin, a molecule that stimulates signal transduction, a transcription factor, an pest or virus-specific antibody, genes that confer herbicide resistance, genes that modulate yield, genes that modulate plant growth and/or plant structure, genes that modulate sterility, genes that increase biomass, genes that increase stand establishment, genes that increase drought or cold tolerance, genes that modulate flowering time, genes that modulate stress tolerance, genes that modulate tolerance to low light, genes that modulate nitrogen use efficiency, genes that modulate seed dormancy and/or germination, genes that modulate the percentages of sugars, genes that modulate the percent of lignin, genes that modulate the percent of cellulose and/or hemicellulose, and genes that modulate the biomass to fuel conversion properties of switchgrass. Genes that can be transformed into switchgrass EG1102 can originate from various species, including, but not limited to, plants, algae, fungi, monera, bacteria, archaeobacteria, protista, and animals. Following transformation of switchgrass target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular switchgrass line using the foregoing transformation techniques could be moved into another line using traditional backcrossing techniques that are well known in the plant breeding arts. For example, a backcrossing approach could be used to move an engineered trait from one variety into another variety, or from a variety containing a foreign gene in its genome into a variety or varieties that do not contain that gene. As used herein, "crossing" can refer to a simple X by Y cross or the process of backcrossing depending on the context.

VI. INDUSTRIAL USES

The seed of switchgrass cultivar EG1102, the plant produced from the seed, the hybrid switchgrass plant produced from the crossing of the variety with any other switchgrass plant, hybrid seed, and various parts of the hybrid switchgrass plant can be utilized for livestock feed, forage, erosion control, and as feedstock for biofuels such as, but not limited to ethanol, butanol, or diesel.

The commercial production of seeds for growing switchgrass plants normally involves four stages, the production of breeder, foundation, certified and registered seeds. Breeder seed is the initial increase of seed of the variety which is developed by the breeder and from which foundation seed is derived. Foundation seed is the second generation of seed increase and from which certified seed is derived. Certified seeds are used in commercial crop production and are produced from foundation or certified seed. Foundation seed normally is distributed by growers or seedsmen as planting stock for the production of certified seed.

Switchgrass variety EG1102 has improved biomass yield and composition properties that result in greater potential gallons of ethanol per acre than other known varieties.

Switchgrass plants provided herein have various uses in the agricultural and energy production industries. For example, switchgrass plants described herein can be used to make animal feed and food products. Such plants, however, are often particularly useful as a biofuel for energy production.

Switchgrass plants described herein often produce higher yields of biomass per hectare, relative to known switchgrass varieties. In some embodiments, such switchgrass plants provide equivalent or even increased yields of biomass per hectare relative to known switchgrass varieties when grown under the same conditions. The switchgrass plants of EG1102 can also be used to provide yield stability at a lower input cost and/or under environmentally stressful conditions such as drought. In some embodiments, plants of EG1102 described herein have a composition that permits more efficient processing into free sugars, and subsequently ethanol, for energy production. In some embodiments, such plants provide higher yields of ethanol, other biofuel molecules, and/or sugar-derived co-products per kilogram of plant material, relative to control plants.

EG1102 will be further described in the following examples, which are not intended to limit the scope of the invention described in the claims.

VII. EXAMPLES

Example 1

Dry Biomass Yield of EG1102

Multi-Location Analysis of Biomass

The present invention, EG1102, was compared to the currently available switchgrass variety Kanlow at several locations. At each location, multiple entries of each variety were planted in the spring of 2007 (unless otherwise indicated) as replicated small plots with 6 replications in a randomized complete block design. Plot size was approximately 9 feet by 20 feet based on available equipment. Each plot was bordered by 2 feet on all sides. To avoid weed growth, the switchgrass varieties were not fertilized in the first year. Harvesting was based on 1) month of full stand senescence; 2) when standing biomass was <25% green; and c) before danger of winter loss. Biomass was harvested only from the center of the plots, leaving at least 1 row or a 3-foot border in each plot. Fresh weight of biomass was measured at harvest. Biomass from each plot was dried to a constant weight before dry weight biomass was recorded. The data for each variety collected in each location is shown in Table 2.

In Table 2, column 1 shows the location, column 2 shows the dry biomass yield in tons/acre for the present invention, EG1102, column 3 shows the dry biomass yield in tons/acre for currently available switchgrass variety Kanlow, column 4 shows the difference in biomass yield in tons/acre between the two varieties and column 5 shows the significant difference.

TABLE 2

Dry biomass yield (ton/acre) for test locations harvested in 2007

| Location | EG1102 | Kanlow | Difference | P |
|---|---|---|---|---|
| Starkville, MS* | 4.4 | 1.3 | 3.1 | <0.001 |
| Champaign, IL | 5.0 | 3.5 | 1.5 | 0.005 |
| El Centro, CA | 4.6 | 3.2 | 1.4 | <0.001 |
| Overton, TX | 1.4 | 0.3 | 1.2 | <0.001 |
| Winnsboro, LA | 2.9 | 1.8 | 1.1 | <0.001 |
| Five Points, CA | 3.2 | 2.4 | 0.9 | 0.011 |
| Ardmore, OK | 1.6 | 0.8 | 0.8 | <0.001 |
| Parsons, KS | 3.5 | 2.8 | 0.6 | 0.037 |
| Stillwater, OK* | 5.4 | 4.9 | 0.4 | 0.376 |
| Garden City, KS | 1.2 | 0.8 | 0.3 | 0.270 |
| Athens, GA | 1.3 | 1.2 | 0.1 | 0.707 |
| Kimberly, ID* | 4.2 | 4.6 | −0.4 | 0.631 |
| Mean | 3.0 | 1.9 | 1.1 | |

*Data collected in 2007 from plants planted in 2006.

As shown in Table 2, the yield difference between the present invention, EG1102, and Kanlow was unexpectedly significant (P<0.05) for eight of the twelve locations where both varieties were established. In all cases EG1102 outyielded Kanlow. The yield difference ranged from 0.6 to 1.3 ton/acre. The highest yield difference occurred at the Starkville, Miss. location where Kanlow yielded relatively low compared to other locations.

Multi-Year Analysis of Biomass

The present invention, EG1102, was compared over four years with two currently available switchgrass varieties, Kanlow and Alamo, for dry biomass yield. The switchgrass varieties were planted in replicated small plots, as described above, at Tifton, Ga. in the spring of 2000. Harvesting and measuring for dry biomass were as described above. The results are shown in Table 3.

In Table 3, column 1 shows the variety and statistical information, column 2 shows the dry biomass yield in kg/ha for each variety for year 2000, column 3 shows the dry biomass yield in kg/ha for each variety for year 2001, column 4 shows the dry biomass yield in kg/ha for each variety for year 2002, column 5 shows the dry biomass yield in kg/ha for each variety for year 2003, and column 6 shows the average dry biomass yield in kg/ha for each variety for all four years.

TABLE 3

Dry biomass yield (kg/ha) for 2000-2003.
Tifton - Established May 2000

| | Harvest Year | | | | |
|---|---|---|---|---|---|
| | 2000 | 2001 | 2002 | 2003 | Average |
| Variety | | | Kg/ha | | |
| EG1102 | 2245 | 20976 | 17693 | 22748 | 15916 |
| Alamo | 2304 | 18088 | 16292 | 21064 | 14437 |
| Kanlow | 2048 | 15380 | 13287 | 20726 | 12860 |
| L.S.D. (p < 0.05) | 1143 | 3457 | 2648 | 3117 | |
| Test Mean | 2629 | 19279 | 16047 | 21780 | |
| CV (%) | 36 | 15 | 14 | 12 | |

As shown in Table 3, the present invention, EG1102, showed an unexpectedly significantly greater dry biomass yield in comparison to Kanlow over a three-year period as plants matured. EG1102 also showed a greater dry biomass yield as compared to Alamo over the three-year period.

The present invention, EG1102, was compared with the currently available switchgrass variety Kanlow for both fresh and dry biomass yield in College Station, Tex. in 2008. The switchgrass varieties were planted as described above for Table 1 and the results are shown in Table 4. In Table 4, column 1 shows the year, column 2 shows the variety, column 3 shows the average fresh biomass in grams per meter squared, column 4 shows the average percent moisture and column 5 shows the average adjusted dry biomass in grams per meter squared.

TABLE 4

Comparison of Fresh and Dry Biomass Yield between EG1102 and Kanlow.

| Year | Variety | Ave. Fresh Biomass (g/m2) | Ave. % Moisture | Ave. Adjusted Dry Biomass (g/m2) |
|---|---|---|---|---|
| 2008 | EG1102 | 414.4633 | 39.31667 | 251.9933 |
| 2008 | Kanlow | 277.7567 | 33.4 | 184.6383 |

As shown in Table 4, EG1102, the present invention had an unexpectedly significantly increased fresh biomass and dry biomass yield over that of the currently available switchgrass variety Kanlow.

In Table 5, the yield in tons per acre for the present invention, EG1102, is compared to the yield for two currently available switchgrass varieties, Alamo and Kanlow, over several different environments: Starkville, Miss., Athens, Ga., Winnsboro, La., Granger, Tex., Ardmore, Okla. and Stillwater, Okla. In the table, column 1 shows the variety, columns 2 through 7 show the yield in tons per acre for each of the six locations and column 8 shows the average for each variety across all locations.

TABLE 5

Comparison of Yield Between EG1102, Alamo and Kanlow over 6 Locations.

| Variety | Starkville, MS | Athens, GA | Winnsboro, LA | Granger, TX | Ardmore, OK | Stillwater, OK | Ave. |
|---|---|---|---|---|---|---|---|
| EG1102 | 10.6 | 12.0 | 8.0 | 11.5 | 6.7 | 6.6 | 9.2 |
| Alamo | 7.4 | 12.6 | 7.7 | 14.1 | 7.5 | 7.9 | 9.5 |
| Kanlow | 2.8 | 7.2 | 5.6 | 10.9 | 6.7 | 6.9 | 6.7 |

As can be seen in Table 5, the present invention, EG1102, had a 138% increase in yield over the currently available switchgrass variety Kanlow over all six locations. This was an unexpected significant difference in yield for EG1102 over Kanlow.

Example 2

Spring Emergence of EG1102

Average Days to Spring Emergence

The present invention, EG1102, was compared with two currently available switchgrass varieties, Alamo and Kanlow, for number of days to spring emergence of new growth from the soil. At Ardmore, Okla., replicated small plots of all three switchgrass varieties were planted in 2007. Individual plants of EG1102, Alamo, and Kanlow were spaced in a honeycomb planting arrangement, and there were 6 randomly selected, spaced plants to represent each of these varieties. Data was collected in spring of 2008 and is shown in Table 5.

In Table 6, column 1 shows the variety, column 2 shows the average number of days to spring emergence of new growth for each variety, and column 3 shows the range of number of days to spring emergence of new growth for each variety.

TABLE 6

Number of Days to Spring Emergence.

| Varieties | Average days to emergence | Range |
| --- | --- | --- |
| EG1102 | 80.2 | 67-83 |
| Alamo | 85.1 | 68-98 |
| Kanlow | 88.7 | 79-93 |

As shown in Table 6, the present invention, EG1102, on average has faster emergence and growth in early spring than do either of the currently available switchgrass varieties Alamo or Kanlow. On average EG1102 has 5 days faster emergence than Alamo and 8 days faster emergence than Kanlow.

Spring Re-Growth Height

The present invention, EG1102, was compared with two currently available switchgrass varieties, Alamo and Kanlow, for spring re-growth plant height as measured in centimeters from the soil level to the top of the plant. The three switchgrass varieties were planted at two locations in replicated small plots as described in Example 1. Plant height measurements were recorded on Apr. 17, 2008 for Ardmore, Okla. and Apr. 29, 2008 for Overton, Tex. The data are shown in Table 7.

In Table 7, column 1 shows the location and planting date, column 2 shows the mean plant height in cm for EG1102, column 3 shows the mean plant height in cm for Alamo, column 4 shows the mean plant height in cm for Kanlow, and column 5 shows the number of plants measured for each variety.

TABLE 7

Comparison of Spring Re-Growth Plant Heights.

| Location and planting date | EG1102 Mean plant height (cm) | Alamo Mean plant height (cm) | Kanlow Mean plant height (cm) | No. plants |
| --- | --- | --- | --- | --- |
| Ardmore 2006 | 39.00 | 36.38 | 33.08 | 6 |
| Ardmore 2007 | 42.00 | 39.67 | 31.25 | 6 |
| Overton 2007 | 91.63 | 90.04 | 74.88 | 6 |

As shown in Table 7, the present invention, EG1102, had a greater plant height in early spring in comparison to Alamo and Kanlow in both testing locations. These data demonstrate a faster rate of spring re-growth in multiple field conditions. Additionally, EG1102 showed more uniform spring re-growth in comparison to Kanlow in field plots.

An additional trial of spring re-growth was performed in 2009 in Ardmore, Okla. comparing the present invention with two currently available switchgrass varieties, Alamo and Kanlow. Spring re-growth was taken in Julian days from January 1 to the first greening, i.e., when the new tillers emerged from the soil. Table 8 shows the results of the spring re-growth trial. Column 1 shows the variety and column 2 shows the number of Julian days from January 1 to the first greening for each switchgrass variety.

TABLE 8

Comparison of Spring Re-Growth between EG1102, Alamo and Kanlow.

| Variety | Days to Spring Re-Growth |
| --- | --- |
| EG1102 | 68.8 |
| Alamo | 61.1 |
| Kanlow | 76.7 |
| LSD (<0.05) | 1.4 |

An additional trial was performed which compared plant vigor as measured by plant height in the spring for the present invention, EG1102 and two currently available switchgrass varieties, Alamo and Kanlow. Table 9 shows the results of this trial. Column 1 shows the varieties, column 2 shows the standing height as measured from the base of the plant to the top of the canopy, column 3 shows the hand held height as measured from the base of the plant to the tip of the flag leaf of the tallest stem on Apr. 8, 2009 and column 4 shows the hand held height as measured from the base of the plant to the tip of the flag leaf of the tallest stem on Apr. 24, 2009.

TABLE 9

Comparison of Spring Vigor as Measured by Plant Height for EG1102, Alamo and Kanlow.

| Variety | Standing Apr. 8, 2009 | Hand Held Apr. 8, 2009 | Hand Held Apr. 24, 2009 |
| --- | --- | --- | --- |
| EG1102 | 46.0 | 55.5 | 85.9 |
| Alamo | 50.6 | 69.6 | 95.4 |
| Kanlow | 35.4 | 38.5 | 70.2 |
| LSD (<0.05) | 2.2 | 6.9 | 3.5 |

Example 3

Other Traits

EG1102 was more tolerant to rust (*Puccinia emaculata*) than Kanlow based on field performance in 2007, 2008 and 2009. Table 10 shows the rust scores for the present invention, EG1102 as compared to the rust score for the currently available switchgrass variety Kanlow over two years and two locations. Individual seedlings were started in a greenhouse using SC-9 Cone-tainers™ (Stuewe and Sons, Corvalis, Oreg.) in March, 2008. Single plants were transplanted in Spring, 2008 and Spring, 2009 in College Station, Tex. and Ardmore, Okla. 50 lbs/N/A were applied at planting and transplants were irrigated for establishment. A total of 90 spaced plants of each variety were grown. The experimental design was a RCBD with six replications; one plot consisted of 15 spaced plants, row spacing was 152 cm, and plants were spaced 76 cm within a row. Plants were scored for rust reaction based on a 1 to 9 scale with 1 being completely susceptible and 9 being completely resistant. The results are shown in Table 10. In table 10, column 1 shows the variety, column 2 shows the rust score for each variety in Texas and column 3 shows the rust score for each variety in Oklahoma.

TABLE 10

Comparison of Rust Resistance for EG1102 and Kanlow over 2 Years and 2 Locations

| Variety | Texas Rust score | Oklahoma Rust score |
|---|---|---|
| EG1102 | 4.2 | 6.0 |
| Kanlow | 2.9 | 5.0 |

As shown in Table 10, the present invention, EG1102, has better rust resistance than switchgrass variety Kanlow over two locations and two years.

Composition

The following chemical composition data was generated by NIR/PLS rapid analysis methods as described in Hames et al., 2003, "Rapid biomass analysis: New tools for compositional analysis of corn stover feedstocks and process intermediates from ethanol production." Applied-Biochemistry-and-Biotechnology 105-108: 5-16, which is incorporated by reference for this purpose. The wet chemical composition analysis was generated by standard laboratory analytical procedures.

The present invention, EG1102, was compared with two currently available switchgrass varieties, Alamo and Kanlow, for chemical composition. Individual seedlings were started in a greenhouse using SC-9 Cone-tainers™ (Stuewe and Sons, Corvalis, Oreg.) in March, 2008. Single plants were transplanted in Jun. 25, 2008 in College Station, Tex. 50 lbs/N/A were applied at planting and transplants were irrigated for establishment. A total of 90 spaced plants of each variety were grown. The experimental design was a RCBD with six replications; one plot consisted of 15 spaced plants, row spacing was 152 cm, and plants were spaced 76 cm within a row. Tissue samples were collected from mature plants in fall 2008.

Table 11 shows the results of the comparison between the present invention, EG1102, and the two currently available switchgrass varieties for selected chemical composition. Column 1 shows the variety, column 2 shows the percent lignin, column 3 shows the percent protein, column 4 shows the percent ash, column 5 shows the percent extractives, column 6 shows the percent glucan, column 7 shows the percent xylan, and column 8 shows the percent sucrose.

TABLE 11

Comparison of Composition Characteristics between EG1102, Alamo and Kanlow.

| Variety | % Lignin | % Protein | % Ash | % Extractives | % Glucan | % Xylan | % Sucrose |
|---|---|---|---|---|---|---|---|
| EG-1102 | 18.1 | 2.3 | 5.3 | 12.6 | 31.7 | 21.2 | 1.3 |
| Alamo | 17.8 | 2.5 | 4.7 | 14.2 | 31.3 | 21.1 | 2.0 |
| Kanlow | 28.1 | 2.1 | 5.3 | 12.4 | 31.4 | 21.2 | 1.2 |

Other Embodiments

It is to be understood that while the variety has been described in conjunction with the detailed description thereof, the foregoing description is intended to illustrate and not limit the scope of the invention, which is defined by the scope of the appended claims. Other aspects, advantages, and modifications are within the scope of the following claims.

Deposit Information

A deposit of the Ceres, Inc proprietary switchgrass cultivar designated EG1102 disclosed above and recited in the appended claims has been made with the American Type Culture Collection (ATCC), 10801 University Boulevard, Manassas, Va. 20110. The date of deposit was Jul. 11, 2008. The deposit of 2,500 seeds was taken from the same deposit maintained by Ceres, Inc. since prior to the filing date of this application. Upon allowance of any claims in this application, all restrictions on the availability to the public of the variety will be irrevocably removed by affording access to a deposit of at least 2,500 seeds of the same variety with the American Type Culture Collection, Manassas, Va., and the deposit is intended to meet all of the requirements of 37 C.F.R. 1.801-1.809. The ATCC accession number is PTA-9364. The deposit will be maintained in the depository for a period of 30 years, or 5 years after the last request, or for the effective life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of switchgrass cultivar EG1102, representative sample of seed of said cultivar was deposited under ATCC Accession No. PTA-9364.

2. A switchgrass plant, or a part thereof, produced by growing the seed of claim 1.

3. Pollen of the plant of claim 2.

4. Progeny of the plant of claim 2, said progeny having all of the physiological and morphological characteristics of switchgrass cultivar EG1102.

5. A switchgrass plant, wherein at least one ancestor of said switchgrass plant is the switchgrass plant of claim 2, and wherein said switchgrass plant possesses all of the physiological and morphological characteristics of switchgrass cultivar EG1102.

6. A tissue culture produced from protoplasts or cells from the plant of claim 2.

7. The tissue culture of claim 6, wherein said cells or protoplasts of the tissue culture are produced from a plant part selected from the group consisting of leaf, pollen, embryo, cotyledon, hypocotyl, meristematic cell, root, root tip, pistil, anther, flower, shoot, stem, and leaf sheath.

8. A switchgrass plant regenerated from the tissue culture of claim 6 wherein the plant has all of the morphological and physiological characteristics of cultivar EG1102.

9. A switchgrass plant regenerated from the tissue culture of claim 6, wherein the plant has all of the composition and conversion characteristics of cultivar EG1102.

10. A method for producing a switchgrass seed comprising crossing two switchgrass plants and harvesting the resultant switchgrass seed, wherein at least one switchgrass plant is the switchgrass plant of claim 2.

11. A switchgrass seed produced by the method of claim 10.

12. A switchgrass plant, or a part thereof, produced by growing said seed of claim 11.

13. A method of producing a transgenic plant, comprising introducing into a cell of the plant of claim 2 an exogenous nucleic acid molecule, said exogenous nucleic acid molecule comprising a regulatory region and a coding region, wherein said regulatory and coding regions are operably linked, and wherein said coding region encodes a polypeptide with an amino acid sequence that alters a plant characteristic as compared to a control plant that does not comprise said exogenous nucleic acid molecule.

14. A method of producing a mutant plant, comprising contacting the plant of claim 2 or a part thereof with a mutagen and selecting for plants having at least one new or altered trait.

15. The method of claim 14, wherein the new or altered trait selected for is herbicide resistance, pest resistance, disease resistance, increased biomass, sterility or partial sterility, increased self-compatibility, plant metabolism, nitrogen use efficiency, increased stress tolerance, yield, stand establishment, drought tolerance, cold tolerance, flowering time, tolerance to low light, seed dormancy and/or germination, plant growth and/or plant structure, modified content of cellulose, lignin, hemicellulose, or sugars in plant tissues.

16. A switchgrass plant produced by the method of claim 13.

17. A method of introducing a desired trait into switchgrass cultivar EG1102, wherein the method comprises:
(a) crossing an EG1102 plant, wherein a representative sample of seed was deposited under ATCC Accession No. PTA-9364, with a plant of another switchgrass cultivar or wild type that comprises a desired trait to produce progeny plants;
(b) selecting one or more progeny plants that have the desired trait to produce selected progeny plants;
(c) crossing the selected progeny plants with the EG1102 plants to produce backcross progeny plants;
(d) selecting for backcross progeny plants that have the desired trait and all of the physiological and morphological characteristics of switchgrass cultivar EG1102; and
(e) repeating steps (c) and (d) three or more times in succession to produce selected fourth or higher backcross progeny plants that comprise the desired trait and all of the physiological and morphological characteristics of switchgrass cultivar EG1102.

18. The method of claim 17, wherein the desired trait is a phenotypic trait, a gene, or a molecular marker.

19. A switchgrass plant produced by the method of claim 17, wherein the plant has the desired trait.

20. The switchgrass plant of claim 19, wherein the desired trait is selected from the group consisting of herbicide resistance, pest resistance, disease resistance, increased biomass, sterility or partial sterility, increased self-compatibility, plant metabolism, nitrogen use efficiency, increased stress tolerance, yield, stand establishment, drought tolerance, cold tolerance, flowering time, tolerance to low light, seed dormancy and/or germination, plant growth and/or plant structure, modified content of cellulose, lignin, hemicellulose, and sugars in plant tissues.

21. The switchgrass plant claim 19, wherein the desired trait is insect resistance and the insect resistance is conferred by a transgene encoding a *Bacillus thuringiensis* endotoxin.

22. The switchgrass plant of claim 19, wherein the desired trait is herbicide resistance and the herbicide resistance is conferred by a transgene encoding a bar gene that confers resistance to bialaphos.

23. The switchgrass plant of claim 19, wherein the desired trait is herbicide resistance and the herbicide resistance is conferred by a transgene encoding a gene that confers resistance to glyphosate.

24. A method of making a switchgrass population, comprising:
(a) crossing two or more switchgrass varieties to make a synthetic population, wherein at least one of said switchgrass varieties is EG1102; and
(b) selecting progeny of said cross that have altered disease resistance, pest resistance, plant metabolism, herbicide resistance, yield, plant growth and/or plant structure, sterility, biomass, stand establishment, drought tolerance, cold tolerance, flowering time, stress tolerance, tolerance to low light, nitrogen use efficiency, seed dormancy and/or germination, altered sugar content, altered lignin content, altered cellulose and/or hemicellulose content, or altered biomass to fuel conversion properties, said progeny constituting said switchgrass population.

25. The method of claim 13, wherein the characteristic altered by the polypeptide is herbicide resistance, pest resistance, disease resistance, increased biomass, sterility or partial sterility, increased self-compatibility, plant metabolism, nitrogen use efficiency, increased stress tolerance, yield, stand establishment, drought tolerance, cold tolerance, flowering time, tolerance to low light, seed dormancy and/or germination, plant growth and/or plant structure, modified content of cellulose, lignin, hemicellulose, or sugars in plant tissues.

* * * * *